United States Patent [19]

Simmons

[11] Patent Number: 5,273,759
[45] Date of Patent: Dec. 28, 1993

[54] METHOD AND COMPOSITION FOR TREATING THE MIGRAINE COMPLEX

[75] Inventor: Donald L. Simmons, Pierrefonds, Canada

[73] Assignee: Lipopharm Inc., St-Laurent, Canada

[21] Appl. No.: 946,133

[22] Filed: Sep. 17, 1992

[51] Int. Cl.$^5$ .................. A61K 9/20; A61K 31/00
[52] U.S. Cl. .................. 424/465; 424/464; 424/489; 514/819; 514/872
[58] Field of Search .................. 424/464, 465, 489; 514/819, 872

[56] References Cited

U.S. PATENT DOCUMENTS 5,053,396 10/1991 Blass .................. 514/45

FOREIGN PATENT DOCUMENTS 1246454 12/1988 Canada .

OTHER PUBLICATIONS

Chemical abstracts 103 (1985) 206302d.
Merck Index, 9th edition (1976), p. 426.

*Primary Examiner*—Paul R. Michl
*Assistant Examiner*—James M. Spear
*Attorney, Agent, or Firm*—Ronald S. Kosie; Robert Brouillette

[57] ABSTRACT

An oral composition comprising in combination acetaminophen, dimenhydrinate and one or more antacid ingredients has been shown to be effective in the treatment of acute migraine attacks.

11 Claims, No Drawings

METHOD AND COMPOSITION FOR TREATING THE MIGRAINE COMPLEX

The present invention generally relates to an oral composition, for the treatment of acute migraine attacks, comprising in combination, an analgesic, an antinauseant and one or more antacid ingredients. More specifically, the present invention relates to an oral tablet medication containing as active ingredients the analgesic acetaminophen and the antinauseant dimenhydrinate.

Migraine attacks affect about 20% of the population and the cause of this debilitating condition is still uncertain today. Migraines may be described as recurring attacks of headache, varying widely in intensity, frequency, and duration. The majority of migraine attacks are also associated with gastrointestinal symptoms which add considerably to the distress and inconvenience caused by the headache. The range of gastrointestinal symptoms in migraine varies from mild nausea to severe vomiting. In a prospective survey of 500 patients attending a specialist outpatient migraine clinic in 1966, Lance and Anthony in Archives of Neurology, volume 15, pages 356–361, found that 96% of patients experienced gastrointestinal symptoms during migraine. The majority of these subjects (93%) reported nausea with 75% of them also experience vomiting. Similarly, in a 1974 survey of 600 acute attacks of migraine, Wilkinson et al in Abstracts of the Sixth Migraine Symposium—Migraine Trust, London 1974 found that nausea occurred in ¾ with vomiting prevalent in nearly ¼ of the attacks. It is obvious that vomiting will reduce the efficacy of orally administered drugs and it has been recently recognized that even if the ingested drugs are retained, they may not be absorbed at the normal rate and that this might be the reason for therapeutic failures seen in migraine patients. Volans in a Nov. 1974 issue of British Medical Journal tested this hypothesis by performing a comparative salicylate absorption study of effervescent aspirin tablets in patients during migraine attacks. He found that the rate of salicylate absorption in migrainous patients was reduced relative to that found in non-migrainous volunteers and, in the same migraine patients when headache-free. This reduced rate of absorption is evidently caused by gastrointestinal stasis and corresponding reduced rate of gastric emptying. Nimmo and coworkers in a Mar. 1974 issue of British Medical Journal have investigated the effects of drug-induced changes on gastric emptying and the corresponding absorption rate of acetaminophen—a drug in which absorption is dependent on the rate of gastric emptying. Propantheline delayed gastric emptying and markedly slowed the absorption of acetaminophen in subjects while the absorption was accelerated by metoclopramide, a drug which stimulates gastric emptying.

Various medications are available for treating migraine attacks. Gawel has reviewed the role of symptomatic and prophylactic drug therapy in a Sept. 1986 issue of Revue Pharmaceutique Canadienne. The infrequent migraine episode is best treated symptomatically, and ergotamine, alone or in combination, is the mainstay of treatment. Unfortunately, 40% of patients find that the side effects preclude its use. Ergotamine is usually combined with an antiemetic such as metoclopramide or domperidone to enhance the effectiveness. Acetylsalicylic acid and acetaminophen, again with an antiemetic (identity not disclosed), can be very effective.

Other combination medications such as FIORINAL ™ (acetylsalicylic acid+caffeine+butalbital with and without codeine) and MERSYNDOL ™ (acetaminophen+codeine+doxylamine) can be extremely useful but care must be taken when prescribing medications containing sedatives and codeine since dependence may result. Some of the new nonsteroidal anti-inflammatory drugs (NSAID's) also possessing analgesic activity such as ibuprofen, naprosyn, ketoprofen, diflunisal, etc., although useful as prophylactic medication, can also be used symptomatically. Some patients respond well to these, while in others there is no effect. The aim of symptomatic therapy is to give enough medication early enough, before headache sets in. Prophylactic treatment has achieved some success with beta blockers (propranolo, nadolol, atenolol), tricyclic antidepressants, amitriptyline, nortriptyline, monoamine oxidase inhibitors (phenelzine) and calcium channel blockers (diltiazem, verapamil) but they all seem to have a limited period of efficacy and the side effects are numerous.

The two non-prescription analgesics most commonly ingested by patients at the onset of a migraine are acetaminophen and acetylsalicylic acid (ASA). Ibuprofen is also useful in treating migraines but there has been some recent adverse publicity concerning possible kidney problems associated with overuse of this drug. Similarly, the gastrointestinal irritation and bleeding problems that arise in many patients following ASA ingestion has led the inventor to concentrate his efforts on the analgesic acetaminophen for the purpose of this disclosure.

SUMMARY OF THE INVENTION

The principal object of the present invention, therefore, bearing in mind the foregoing comments, is to provide an oral composition designed for the relief of acute migraine attacks or, in other words, for the symptomatic relief of the headache and nausea characteristic of the migraine condition.

Another object of the invention is to provide novel compositions comprising in combination an analgesic and an antinauseant together with one or more antacid ingredients, the analgesic comprising acetaminophen and the antinauseant comprising dimenhydrinate. The compositions of the present invention may contain such components in any effective proportions sufficient to provide relief of migraine headaches.

A further object of the invention is the provision of an effective method of alleviating the pain characteristic of the migraine complex, consisting in the administration of oral compositions including in admixture the above mentioned analgesic and an antinauseant together with one or more antacid substances.

In particular, the present invention, in accordance with one aspect, provides an oral composition for the treatment of acute migraine attacks comprising a medicament component consisting of acetaminophen, dimenhydrinate and at least one antacid ingredient.

In accordance with the present invention, the composition may include one or more pharmaceutically acceptable additives selected from the group consisting of carriers and adjuvants.

The present invention, in accordance with another aspect, provides a method of treating the pain characteristic of the migraine complex comprising administering an oral composition comprising a medicament component consisting of acetaminophen, dimenhydrinate and at least one antacid ingredient.

A further object of the invention is the provision of an effective method of alleviating the pain characteristic of the migraine complex, consisting in the administration of oral compositions including in admixture the above mentioned analgesic and an antinauseant together with one or more antacid substances.

In accordance with the present invention, the antacid substance may be selected from the group comprising magnesium hydroxide, aluminum hydroxide, calcium carbonate, magnesium carbonate and aluminum hydroxide/magnesium carbonate co-dried gel.

In accordance with the present invention, the components of the composition may, for example, be used in an oral dosage form (e.g. tablet) in amounts as follows:
- analgesic component—from about 100 mg to about 500 mg
- antinauseant component—from about 10 mg to about 50 mg
- antacid component—from about 100 mg to 500 mg.

It should be emphasized, however, that the amounts of the various components may vary from the above amounts; the amounts may be less than or greater than the amounts which are given above by way of example only.

Without limiting the scope of the present invention, the relative amounts of an example composition may, for example, be as follows: acetaminophen 325 mg, dimenhydrinate 25 mg, aluminum hydroxide 100 mg and magnesium hydroxide 50 mg.

The compositions in accordance with the present invention may, if desired, also include the following additional ingredients: a glidant, a lubricant, a disintegrating agent and a filler (and, if also desired, a pigmenting material).

In accordance with a particular embodiment of the present invention, there is provided a composition, as defined herein, which comprises acetaminophen, dimenhydrinate, magnesium hydroxide and aluminum hydroxide.

In accordance with an advantageous feature of the present invention an anti-migraine formulation according to the invention may be prepared in the form of a fast disintegrating oral tablet which may contain, as active ingredients, the following: acetaminophen (e.g. 325 mg); dimenhydrinate (e.g. 25 mg); aluminum hydroxide (e g 100 mg); and magnesium hydroxide (e.g. 50 mg).

The dosage may be one or two tablets immediately at the onset of an attack followed, if needed, by one or two tablets every four hours, not to exceed 8 tablets in a 24 hour period.

In accordance with the present invention a composition may, for example, comprise
- Acetaminophen,
- Dimenhydrinate,
- Magnesium Hydroxide,
- Aluminum Hydroxide Dried Gel,
- Microcrystalline Cellulose,
- Croscarmellose Sodium,
- Colloidal Silica and
- Magnesium Stearate.

In accordance with the present invention a composition may, for example, also comprise
- Acetaminophen,
- Dimenhydrinate,
- Magnesium Hydroxide,
- Aluminum Hydroxide Dried Gel,
- Microcrystalline Cellulose,
- Pregelatinized Starch,
- Croscarmellose Sodium,
- Colloidal Silica and
- Magnesium Stearate.

It is believed that the combination herein of the above analgesic, and the above antinauseant with one or more antacids does not exist and has never been prescribed for the treatment of migraine attacks.

However, analgesics have been combined with antacids. For example, Whitehall's ARTHRITIS PAIN FORMULA TM contains ASA 486 mg and aluminum hydroxide 20 mg and magnesium hydroxide 60 mg; Bristol-Myers ARTHRITIS STRENGTH BUFFERIN TM has ASA 486 mg along with magnesium carbonate and aluminum glycinate; Rorer's ASCRIPTIN TM has ASA 325 mg, magnesium hydroxide 75 mg and aluminum hydroxide 75 mg; Glenbrook's VANQUISH CAPLET TM contains ASA 227 mg, acetaminophen 184 mg, magnesium hydroxide 50 mg, aluminum hydroxide 25 mg and caffeine 33 mg.

Analgesics have also been combined with anti-emetics or antinauseants with and without codeine. For example, both ASA and acetaminophen have been combined with metoclopramide and are commercially available in the United Kingdom. Bayer market the products MIGRAVESS TM and MIGRAVESS FORTE TM which are presented as soluble scored tablets containing either ASA 325 mg or ASA 450 mg, and metoclopramide hydrochloride 5 mg. Beecham market a product PARAMAX TM which is available in both tablets and sachets and both contain acetaminophen 500 mg and metoclopramide hydrochloride 5 mg.

These products were observed by Steiner and Rose to work reasonably well when administered to migraine patients attending the Princess Margaret Migraine Clinic in London, England. These authors reported their findings in a review article on problems encountered in the assessment of treatment of headache and migraine which appeared in the textbook, Headache, Publishers W. B. Saunders, 1988. For first-line acute therapy for migraine at the Clinic, these authors use simple analgesics such as ASA or acetaminophen, or one of several NSAID's, preferably in a soluble formulation, with metoclopramide to improve gastric emptying whether there is nausea or not. Parenteral metoclopramide was administered to overcome gastric stasis. Another product widely used in the United Kingdom for treating migraine is MIGRALEVE TM or MIGRALIFT TM which is marketed by International Laboratories and contains the antiemetic buclizine hydrochloride 6.25 mg, paracetamol or acetaminophen 500 mg and codeine phosphate 8 mg.

Prior to the introduction time of the systemic anti-ulcer agents cimetidine and ranitidine, any gastric ulcer patient who simultaneously suffered from headaches and motion sickness obviously had cause to combine these various medications.

The oral composition of the present invention may be prepared in the form of a capsule or a direct compression or granulated tablet as exemplified below. The composition of the present invention may, if desired, also include as component(s) thereof, pharmaceutically acceptable carriers, diluents, excipients, adjuvants, etc.. The composition may, for example, contain other tablet glidants, lubricants, disintegrating agents, fillers, etc., which may be used in preparing the tablets.

In accordance with an advantageous feature of the present invention a tablet, formulated in accordance with the present invention, may, if desired, include a rapid disintegration component as well as the antacid component(s); this combination of components has an advantageous effect on gastrointestinal motor activity. Alkalinization of the gastric contents increases gastric motility through the action of gastrin and therefore would alleviate the gastric stasis that occurs with the onset of migraine attacks. The net effect of this enhanced gastric motility is a rapid and unimpeded delivery of acetaminophen and dimenhydrinate to the area of the small intestine for immediate dissolution, absorption, and distribution. These drugs are therefore biologically available for treating any pain or nausea that might develop during the migraine episode.

With respect to the disintegrant components, the oldest and most popular disintegrant which has been used, is corn or potato starch. However, a new group of materials known as "super disintegrants" have gained in popularity. While starches, clays, aliginates, etc., may require 5 to 10% concentrations to be effective, these newer disintegrants may be effective at 0.5 to 4% concentration. Croscarmellose sodium, crospovidone and sodium starch glycolate are representative of these new disintegrants of which the former is the most effective, swelling in water in less than 10 seconds (see Remington's Pharmaceutical Sciences, 18th Edition, page 1637).

Samples of a formulation in accordance with the present invention (see example 1 below) in the form of tablets have been given to women who have suffered from classic or common migraine attacks for many years and who have been prescribed all of the known medications for treating this affliction. Without exception, the women have stated that this new tablet formulation is superior to other medications, particularly when taken at the onset of an attack.

Prior to marketing this tablet formulation, the Health Protection Branch (HPB) of Canada requested that a preclinical New Drug Submission be filed with their agency. Consequently, the company is currently operating under an HPB approved clinical protocol which will confirm the safety and efficacy of these tablets. The title of the protocol is "A Double-blind Crossover Study of AFTA Tablets versus Placebo in the symptomatic Treatment of Acute and Common Migraine"; AFTA Tablets being tablets formulated in accordance with the present invention. The principal investigator in this trial is Dr Michel Lebel, MD, FRCP(C), a neurologist at the Centre Hospitalier, St-Vincent de Paul, Sherbrooke, Quebec, Canada as well as Associate Professor of Clinical Instruction, Faculty of Medicine, at the University of Sherbrooke. This clinical trial is in progress.

The following examples are given by way of illustration only and not of limitation.

EXAMPLE 1

A direct compression formulation for 10,000 tablets containing the following ingredients is prepared as described below:

| | |
|---|---|
| Acetaminophen (direct compression grade, 90%) | 3,620 gms |
| Dimenhydrinate | 250 gms |
| Magnesium Hydroxide High Density Grade | 500 gms |

-continued

| | |
|---|---|
| Aluminum Hydroxide Dried Gel High Density Grade | 1,000 gms |
| Microcrystalline Cellulose (Avicel PH-102) | 1,250 gms |
| Croscarmellose Sodium (Ac-Di-Sol) | 80 gms |
| D&C Yellow #10 Lake (15%) | 4 gms |
| Collodial Silicon Dioxide (Aerosil 200) | 25 gms |
| Magnesium Stearate | 80 gms |

Approximately one-half of the microcrystalline cellulose is intimately mixed with magnesium hydroxide, aluminum hydroxide dried gel and the direct compression grade acetaminophen. The remaining ingredients are intimately mixed separately and screened manually through a #40 stainless steel screen. The two portions are then mixed together and compressed using a suitable tablet press to a tablet weight of about 681 mg.

EXAMPLE 2

A granulation formulation for 10,000 tablets containing the following ingredients is prepared as described below:

| | |
|---|---|
| Acetaminophen (direct compression grade, 90%) | 3,620 gms |
| Dimenhydrinate | 250 gms |
| Magnesium Hydroxide High Density Grade | 500 gms |
| Aluminum Hydroxide Dried Gel High Density Grade | 1,000 gms |
| Microcrystalline Cellulose (Avicel PH-102) | 400 gms |
| Pregelatinized Starch (Starch 1500) | 460 gms |
| Purified Water Q S | |
| Croscarmellose Sodium (Ac-Di-Sol) | 40 gms |
| D&C Yellow #10 Lake (15%) | 4 gms |
| Collodial Silicon Dioxide (Aerosil 200) | 20 gms |
| Magnesium Stearate | 60 gms |

The same general procedure used in Example 1 was followed here except the antacid components were granulated using the pregelatinized starch and purified water (water being used in an amount sufficient to make a starch-water mixture comprising 15% by weight starch) and the resulting wet granules spread on trays and dried in a suitable oven. The dried granules were sized and mixed with the remaining powders and compressed to a tablet weight of about 635 mg.

EXAMPLE 3

Single table formulation(s) may be as follows:

| Ingredients | I mg/tab. | II mg/tab. |
|---|---|---|
| 1. Acetaminophen, USP | 325 | 325 |
| 2. Dimenhydrinate, USP | 25 | 25 |
| 3. Magnesium Hydroxide, USP | 50 | 50 |
| 4. Aluminum Hydroxide Dried Gel, USP | 100 | 100 |
| 5. Microcrystalline cellulose, NF | 125 | 40 |
| 6. Pregelatinized Starch, NF | | 46 |
| 7. Croscarmellose Sodium, NF | 8 | 4 |
| 8. D&C Yellow #10 Lake | 0.4 | 0.4 |
| 9. Colloidal Silicon Dioxide, NF | 2.5 | 2.0 |
| 10. Magnesium Stereate, NF | 8 | 6 |

An alternate formulation II, in which the antacid components are granulated with starch paste, was prepared in the event problems might be encountered in high-speed tablet presses with direct compression formula I.

The essential characteristics of the present invention will readily be understood and appreciated by persons skilled in the art, and such persons will without difficulty be able to devise modifications, within the scope of the disclosure, for the purpose of adapting the invention to various conditions and circumstances, and will at all times be aware that any such modifications fall within the scope of the appended claims.

The embodiments of the invention in which an exclusive property or privilege is claimed are defined as follows:

1. An oral composition for the treatment of acute migraine attacks comprising a medicament component consisting of acetaminophen, dimenhydrinate and at least one antacid ingredient.

2. A composition according to claim 1, wherein the antacid ingredient is selected from the group consisting of magnesium hydroxide, aluminum hydroxide, calcium carbonate, magnesium carbonate and aluminum hydroxide/magnesium carbonate co-dried gel.

3. A composition according to claim 1 wherein the medicament component consists of acetaminophen, dimenhydrinate, magnesium hydroxide and aluminum hydroxide.

4. An oral composition for the treatment of acute migraine attacks comprising a medicament component consisting of acetaminophen, dimenhydrinate and at least one antacid ingredient, said composition including one or more phyarmaceutically acceptable additives selected from the group consisting of carriers and adjuvants.

5. A composition according to claim 4 whereinsaid one or more pharmaceutically acceptable additives are selected from the group consisting of a glidant, a lubricant, a disintegrating agent, a filler, and a pigmenting material.

6. A composition according to claim 5, wherein the antacid ingredient is selected from the group consisting of magnesium hydroxide, aluminum hydroxide, calcium carbonate, magnesium carbonate and aluminum hydroxide/magnesium carbonate co-dried gel.

7. A composition according to claim 6 wherein said one or more pharmaceutically acceptable additives are selected from the group consisting of a glidant, a lubricant, a disintegrating agent, a filler, and a pigmenting material.

8. A composition according to claim 4, wherein the medicament component consists of acetaminophen, dimenhydrinate, magnesium hydroxide and aluminum hydroxide.

9. A composition according to claim 8 wherein said one or more pharmaceutically acceptable additives are selected from the group consisting of a glidant, a lubricant, a disintegrating agent, a filler, and a pigmenting material.

10. The method of treating the pain characteristic of the migraine complex comprising administering an oral composition comprising a medicament component consisting of acetaminophen, dimenhydrinate and at least one antacid ingredient.

11. The method of treating the pain characteristic of the migraine complex according to claim 10, wherein the antacid ingredient is selected from the group consisting of magnesium hydroxide, aluminum hydroxide, calcium carbonate, magnesium carbonate, and aluminum hydroxide/magnesium carbonate co-dried gel.

* * * * *